United States Patent
Ye et al.

(10) Patent No.: US 9,440,918 B2
(45) Date of Patent: Sep. 13, 2016

(54) METHOD FOR PURIFYING (S)-OXIRACETAM

(75) Inventors: Lei Ye, Chongqing (CN); Zuyuan Rong, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 14/237,891

(22) PCT Filed: Apr. 23, 2012

(86) PCT No.: PCT/CN2012/074501
§ 371 (c)(1),
(2), (4) Date: Feb. 10, 2014

(87) PCT Pub. No.: WO2013/020388
PCT Pub. Date: Feb. 14, 2013

(65) Prior Publication Data
US 2014/0171659 A1    Jun. 19, 2014

(30) Foreign Application Priority Data
Aug. 11, 2011 (CN) .......................... 2011 1 0229933

(51) Int. Cl.
C07D 207/273 (2006.01)

(52) U.S. Cl.
CPC ................................ C07D 207/273 (2013.01)

(58) Field of Classification Search
CPC ................................................ C07D 207/273
See application file for complete search history.

(56) References Cited

U.S. PATENT DOCUMENTS

| | | | |
|---|---|---|---|
| 4,686,296 A * | 8/1987 | Iriuchijima et al. .......... 548/544 |
| 2007/0185337 A1 | 8/2007 | Kim et al. | |

FOREIGN PATENT DOCUMENTS

| | | |
|---|---|---|
| CN | 1956953 A | 5/2007 |
| CN | 101367757 A | 2/2009 |
| CN | 101575309 A | 11/2009 |
| CN | 102050774 A | 5/2011 |
| CN | 102101836 A | 6/2011 |
| CN | 102249974 A | 11/2011 |
| CN | 102249975 A | 11/2011 |
| WO | WO 2005115978 * | 12/2005 .......... C07D 207/273 |

OTHER PUBLICATIONS

Myerson (Handbook of Industrial Crystallization, 2nd ed. (2002), 313 pages).*
Mullin (Crystallization, 4th ed (2001), 594 pages).*
Anderson ("Chapter 11: Tools for Purifying the Product: Column Chromatography, Crystallization and Reslurrying," Practical Process Research & Development, 2000, pp. 223-247).*
Hurst et al., "Accurate quantification of quartz and other phases by powder X-ray diffractometry," Analytica Chimica Acta, 337 (1997) 233-52.
Campbell Roberts, et al. "Quantitative analysis of mannitol polymorphs. X-ray powder diffractometry—exploring preferred orientation effects" J. Pharm. Biomed. Anal. 28 (2002) 1149-59.
Morissette et al., "High-throughput crystallization: Polymorphs, salts, co-crystals and solvates of pharmaceutical solids", Advanced Drug Delivery Reviews 56 (2004) 275-300.
Tiwari et al., "Quantification of olanzapine polymorphs using powder X-ray diffraction technique" J. Pharm. Biomed. Anal., 43 (2007) 865-72.
Fabbiani et al. "An exploration of the polymorphism of piracetam using high pressure", CrystEngComm, 7(29) (2005), 179-186.
Chen, et al., "Solid-State Behavior of Cromolyn Sodium Hydrates", J. Pharm. Sci., (1999) v. 88, p. 1191.
Brittain, "Polymorphism in Pharmaceutical Solids," vol. 95, 1999, Taylor & Francis, Harry G. Brittain (Ed.), 427 pages.
Dyer, Ion Exchange, Encyclopedia of Separation Science, 2000, pp. 156-173.
International Search Report dated Jul. 26, 2012 for PCT/CN2012/074516.

* cited by examiner

*Primary Examiner* — Robert Havlin
(74) *Attorney, Agent, or Firm* — Knobbe, Martens, Olson & Bear LLP

(57) ABSTRACT

A method for purifying (S)-oxiracetam is disclosed. Crude (S)-oxiracetam with the purity of 89% is dissolved in water; the solution is allowed to stand for 1 to 3 days at 0° C. to 18° C.; a colorless transparent crystal is precipitated; the solution is filtered and top-washed with cold water to 0° C. to 5° C.; and the product is dried in vacuum to obtain high-purity (S)-oxiracetam.

8 Claims, No Drawings

METHOD FOR PURIFYING (S)-OXIRACETAM

FIELD OF THE INVENTION

The present invention relates to a crystal purification method, in particular to the method for purifying (S)-4-hydroxy-2-oxo-1-pyrrolidine acetamide.

BACKGROUND OF THE INVENTION

Oxiracetam (Olaxiracetam) is a nootropic drug which was first synthesized by Smithkline Beecham (Italia) and launched in Italy in 1987. (S)-oxiracetam is a single enantiomer with a chemical name of (S)-4-Hydroxy-2-oxo-1-pyrrolidineacetamide (hereinafter referred to as "(S)-oxiracetam).

Oxiracetam is capable of promoting the synthesis of phosphorylcholine and phosphoryl ethanol, promoting brain metabolism, and providing a stimulating effect to specific central nervous pathway through blood brain barrier to improve the ATP/ADP ratio of the brain and enhance the synthesis of brain protein and nucleic acid, so as to improve the memory and learning ability of mentally retarded patients, and the drug itself is not vascular active or causes any stimulation to the central nervous system, but this drug has a persistent promoting effect on learning and memory. P.R.C. Pat. Nos. CN1513836, CN1948285 and CN101121688 have disclosed methods for synthesizing a racemate composed of two isomers, respectively: L-Oxiracetam and R-Oxiracetam. P.R.C. Pat. Nos. CN101367757 and CN101575309 have disclosed methods for preparing L-Oxiracetam. P.R.C. Pat. Nos. CN1424034, CN1555794, CN1562000 and CN101152175 have disclosed methods for preparing Oxiracetam injection agent, dispersible tablets, and lyophilized as well as a new formulation. International Pat. No. WO 93/06826 has discloses a method for improving the treatment effect with regard to intelligence by Oxiracetam. However, the purification process of (S)-oxiracetam is relatively complicated or the purity of the product is relatively low, so that it is difficult to obtain high-purity (S)-oxiracetam at a low cost by a simple manufacturing process.

SUMMARY OF THE INVENTION

Therefore, it is a primary objective of the present invention to provide a method of purifying (S)-oxiracetam in order to prepare (S)-oxiracetam with low impurity (or high purity), and the method is simple and low-cost.

To achieve the aforementioned objective, the present invention provides a method of purifying (S)-oxiracetam, comprising the following steps:

1. Dissolve Crude (S)-oxiracetam in water; allow the solution to stand still at 0° C. to 18° C. for 1 to 3 days; and precipitate the solution to obtain a colorless transparent crystal.
2. Filter and top-wash the colorless transparent crystal with cold water from 0° C. to 5° C.
3. Dry the product in vacuum to obtain high-purity (S)-oxiracetam.

To thoroughly precipitate the (S)-oxiracetam dissolved in water, the ratio of mass to volume (g/ml) of the crude (S)-oxiracetam and water adopted in the step 1 is preferably 1:0.5~2, and more preferably 1:0.8, and the temperature for the solution to stand still as described in the step 1 is preferably 5° C. to 15° C., and more preferably 11° C.

To further improve the purity of the final product of (S)-oxiracetam, the temperature of the ice water used in the step 2 is preferably at 2° C. to 4° C. and more preferably 3° C., and the ratio of mass to volume (g/ml) of the precipitated crystal and ice water is preferably 1:1~2.

Preferably, the drying in vacuum as described in the step 3 takes place at a temperature of 26° C. to 28° C. for 4~5 hours.

Specifically, a method of purifying (S)-oxiracetam comprises the following steps:

1. Dissolve Crude (S)-oxiracetam (with purity ≤89%) in water; allow the solution to stand still at 11° C. for 26~28 hours; and precipitate the solution to obtain a colorless transparent crystal, wherein the ratio of mass to volume (g/ml) of the crude (S)-oxiracetam and water is 1:0.8.
2. Filter and top-wash the colorless transparent crystal with cold water, wherein the ratio of mass to volume (g/ml) of the precipitated crystal and ice water is preferably 1:1~2, and the ice water is at 3° C.
3. Dry the product in vacuum at 26° C. to 28° C. for 4~5 hours to obtain high-purity (S)-oxiracetam.

The present invention has the following advantages and effects: (S)-oxiracetam has a high solubility, so that it will be dissolved quickly by water, and most people believe that it is infeasible to use water as a solvent to purify (S)-oxiracetam. The inventor of the present invention also had the same thought at the beginning, and thus adopted organic solvents to purify (S)-oxiracetam. After conducting extensive experiments, the inventor of the present invention discovered that using water as a solvent to purify crude (S)-oxiracetam of 89% can improve the HPLC purity to 98%~98.4%. In addition, this simple method has the features of mild control conditions, low production cost, free of pollution caused by organic solvents, eco-friendly, and applicable for large-scale industrial production.

DESCRIPTION OF THE PREFERRED EMBODIMENTS

The aforementioned and other objectives and advantages of the present invention will become clearer in light of the following detailed description of an illustrative embodiment of this invention. It is intended that the embodiments disclosed herein are to be considered illustrative rather than restrictive.

Preferred Embodiment 1

A method for purifying (S)-oxiracetam comprises the following steps: Dissolve 1 g of crude (S)-oxiracetam (with a purity of 89%) in 0.8 ml of water, allow the solution to stand still at 11° C. for 28 hours, and precipitate the solution to obtain a colorless transparent crystal. Filter and top-wash the colorless transparent crystal with 1 ml of cold water at 3° C. Dry the product at 26° C.~28° C. in vacuum for 4~5 hours to obtain 0.7 g of the colorless transparent crystal with HPLC purity of 98.4%.

More specifically, the method of preparing the aforementioned (S)-oxiracetam comprises the following steps:

(a) Put 28.50 g of glycinamide hydrochloride, 20.65 g of sodium bicarbonate and 200 ml of anhydrous ethanol into three reaction flasks respectively, control the pH value to approximately 7.4, and stir the solution to increase the temperature until a reflux occurs;

(b) Drop 39.08 g of S-4-chloro-3-hydroxybutyate after the reflux has taken place for 2 hours. In the dropping process, 5 patches of the remaining of 20.65 g the sodium bicarbonate are added gradually, and the pH value is checked and controlled for each time when the alkaline is added, so as to ensure the pH value ≤8.5.

(c) After the dropping, (S)-4-chloro-3-hydroxybutyrate is refluxed for 24 hours until the HPLC testing product (S)-4-hydroxy-2-oxo-1-pyrrolidinyl acetamide content reaches 74%, and the crude (S)4-hydroxy-2-oxo-1-pyrrolidinyl acetamide is obtained after the heating, filtering and concentrating processes.

(d) The above-mentioned crude product is dissolved in 50 ml of water, and processed by 500 ml of 001×7 strong acidic styrene cation-exchange resin, and the product is collected. Use 201×7 strong alkaline styrene anion-exchange resin for neutralization and collect the resulted aqueous solution. The neutralization is determined to be finished when the pH value of the solution reaches 7.0±0.1.

Preferred Embodiment 2

A method for purifying (S)-oxiracetam, comprising the following steps:

Dissolve 8 Kg of crude (S)-oxiracetam (with a purity of 89%) in 16 liters of water, allow the solution to stand still at 15° C. for 30 hours, and precipitate the solution to obtain a colorless transparent crystal. Filter and top-wash the colorless transparent crystal with 10.5 liters of cold water at 4° C. Dry the product at room temperature in vacuum for 5 hours to obtain 5 Kg of the colorless transparent crystal with HPLC purity of 98.2%.

Preferred Embodiment 3

A method for purifying (S)-oxiracetam, comprising the following steps:

Dissolve 1 Kg of crude (S)-oxiracetam (with a purity of 89%) in 0.6 liter of water, allow the solution to stand still at 8° C. for 25 hours, and precipitate the solution to obtain a colorless transparent crystal. Filter and top-wash the colorless transparent crystal with 0.8 liter of cold water at 0° C. Dry the product at 30° C. in vacuum for 4 hours to obtain 0.6 Kg of the colorless transparent crystal with HPLC purity of 98.3%.

While the invention has been described by means of specific embodiments, numerous modifications and variations could be made thereto by those skilled in the art without departing from the scope and spirit of the invention set forth in the claims.

What is claimed is:

1. A method of purifying (S)-oxiracetam, comprising:
    dissolving crude (S)-oxiracetam in water, then treating with a 001×7 strong acidic styrene cation-exchange resin and a 201×7 strong alkaline styrene anion-exchange resin;
    after said treating with the resins, dissoving the crude (S)-oxiracetam in water so as to provide a solution, allowing the solution to stand still at 0° C. to 18° C. for 1 to 3 days, and precipitating the solution to obtain a colorless transparent crystal, wherein a ratio of mass to volume (g/ml) of the crude (S)-oxiracetam and the water used in said dissolving to provide the solution is 1:0.5 to 2;
    filtering and top-washing the colorless transparent crystal with cold water from 0° C. to 5° C. so as to provide a product; and
    drying the product in vacuum to obtain high-purity (S)-oxiracetam;
    wherein said method is performed without any organic solvent.

2. The method of purifying (S)-oxiracetam according to claim 1, wherein a temperature set for the water to stand in said dissolving to provide the solution is from 5° C. to 15° C.

3. The method of purifying (S)-oxiracetam according to claim 2, wherein the ratio of mass to volume (g/ml) of the crude (S)-oxiracetam and the water used in said dissolving to provide the solution is 1:0.8, and the temperature set for the water to stand still in said dissolving to provide the solution is 11° C.

4. The method of purifying (S)-oxiracetam according to claim 1, wherein the cold water used in said filtering has a temperature of 2° C. to 4° C., and a ratio of mass to volume (g/ml) of the precipitated crystal and the cold water said dissolving is 1:1 to 2.

5. The method of purifying (S)-oxiracetam according to claim 4, wherein the cold water used in said filtering has a temperature of 3° C.

6. The method of (S)-oxiracetam according to claim 1, wherein the drying in vacuum takes place at a temperature of 26° C. to 28° C. for 4 to 5 hours.

7. The method of purifying (S)-oxiracetam according to claim 1, comprising:
    dissolving crude (S)-oxiracetam in water, then treating with a 001×7 strong acidic styrene cation-exchange resin and a 201×7 strong alkaline styrene anion-exchange resin;
    after said treating with the resins, dissolving crude (S)-oxiracetam (purity≤89%) in water so as to provide a solution, allowing the solution to stand still at 11° C. for 26 to 28 hours, and precipitating the solution to obtain a colorless transparent crystal, wherein a ratio of mass to volume (g/ml) of the crude (S)-oxiracetam and water is 1:0.8;
    filtering and top-washing the colorless transparent crystal with cold water from 0° C. to 5° C. so as to provide a precipitated crystal; and
    drying the precipitated crystal in vacuum at 26° C. to 28° C. for 4 to 5 hours to obtain high-purity (S)-oxiracetam.

8. The method of purifying (S)-oxiracetam according to claim 7, wherein, in said filtering, a ratio of mass to volume (g/ml) of the precipitated crystal and the cold water is 1:1 to 2, and the cold water is at 3° C.

* * * * *